(12) United States Patent
Won et al.

(10) Patent No.: US 8,524,215 B2
(45) Date of Patent: Sep. 3, 2013

(54) ABSORBABLE PEG-BASED HYDROGELS

(75) Inventors: Chee-Youb Won, Belle Mead, NJ (US); Helen Cui, Basking Ridge, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 4 days.

(21) Appl. No.: 13/193,958

(22) Filed: Jul. 29, 2011

(65) Prior Publication Data

US 2012/0027775 A1 Feb. 2, 2012

Related U.S. Application Data

(60) Provisional application No. 61/369,818, filed on Aug. 2, 2010.

(51) Int. Cl.
*A61K 31/74* (2006.01)

(52) U.S. Cl.
USPC ....................................... 424/78.31

(58) Field of Classification Search
None
See application file for complete search history.

(56) References Cited

U.S. PATENT DOCUMENTS

| | | | |
|---|---|---|---|
| 6,362,276 B1 * | 3/2002 | Harris et al. | 525/54.1 |
| 6,624,245 B2 | 9/2003 | Wallace | |
| 6,858,736 B2 * | 2/2005 | Nho et al. | 546/290 |
| 7,018,624 B2 * | 3/2006 | Harris | 424/78.3 |
| 7,265,186 B2 * | 9/2007 | Zhao | 525/419 |
| 7,291,673 B2 * | 11/2007 | Hubbell et al. | 525/50 |
| 7,312,301 B2 * | 12/2007 | Fang et al. | 528/391 |
| 7,560,112 B2 | 7/2009 | Chen | |
| 7,744,861 B2 * | 6/2010 | Zhao et al. | 424/78.17 |
| 7,955,788 B2 * | 6/2011 | Zilla et al. | 435/1.1 |
| 2002/0019340 A1 * | 2/2002 | Bentley et al. | 514/2 |
| 2004/0076602 A1 * | 4/2004 | Harris | 424/78.3 |
| 2004/0096507 A1 * | 5/2004 | Kwang et al. | 424/486 |
| 2004/0147466 A1 | 7/2004 | Barman | |
| 2006/0233854 A1 * | 10/2006 | Seliktar et al. | 424/422 |
| 2006/0233855 A1 * | 10/2006 | Seliktar et al. | 424/422 |
| 2008/0025943 A1 | 1/2008 | Michal | |
| 2008/0131509 A1 | 6/2008 | Hossainy | |
| 2009/0074704 A1 * | 3/2009 | Zhao et al. | 424/78.3 |
| 2009/0252781 A1 * | 10/2009 | Sawhney et al. | 424/427 |
| 2010/0004424 A1 * | 1/2010 | Fang et al. | 528/391 |
| 2010/0292146 A1 * | 11/2010 | Seibl et al. | 514/8.8 |
| 2011/0033543 A1 * | 2/2011 | Kiick et al. | 424/484 |
| 2011/0104280 A1 * | 5/2011 | Hnojewyj | 424/486 |
| 2011/0224724 A1 * | 9/2011 | Lu et al. | 606/1 |
| 2011/0286926 A1 * | 11/2011 | Sinko et al. | 424/9.1 |
| 2012/0026458 A1 * | 2/2012 | Qiu et al. | 351/160 H |
| 2012/0129954 A1 * | 5/2012 | Falcone et al. | 514/781 |
| 2012/0177611 A1 * | 7/2012 | Blau et al. | 424/93.7 |
| 2012/0314185 A1 * | 12/2012 | Bauman et al. | 351/159.33 |

FOREIGN PATENT DOCUMENTS

| | | |
|---|---|---|
| EP | 0464163 | 4/1995 |
| EP | 2014256 | 1/2009 |
| WO | WO 00/78285 | 12/2000 |
| WO | WO 2004/060967 A1 | 7/2004 |
| WO | WO 2008069919 | 6/2008 |
| WO | WO 2009132153 | 10/2009 |

OTHER PUBLICATIONS

Huaiqing Yu, Zeng-guo Feng, Ai-ying Zhang, Ling-gang Sun and Lijun Qian. Synthesis and characterization of three-dimensional crosslinked networks based on self-assemly of a-cyclodextrins with thiolated 4-arm PEG using a three-step oxidation. Soft Matter, 2006, 2, 343-349.*
PCT International Search Report for Application No. PCT/US2011/046107 dated Nov. 15, 2011.
Metters, Andrew, et al., Network Formation and Degradation Behavior of Hydrogels formed by Michael-type addition reactions. Biomacromolecules, 2005, vol. 6, pp. 290-301.
Tector, Alfred, J. et al., The Internal Mammary Artery Graft, JAMA, Nov. 13, 1981; vol. 246, No. 19, pp. 2181-2183.
Mizuhiro, Arima, MD., Serial Angiographic Follow-up Beyond 10 Years After Coronary Artery Bypass Grafting, Circulation Journal, vol. 69, Aug. 2005, pp. 896-902.
Horstick, Georg, Resistance of the Internal Mammary Artery to Restenosis: A Histomorphologic Study of Various Porcine Arteries, S. Karger AG, Basel 2007, pp. 45-63.
Zustiak, Silviya, et al., Hydrolytically Degradable Poly(Ethylene Glycol) Hydrogel Scaffolds with Tunable Degradation and Mechanical Properties, Biomacromolecules 2010, vol. 11, pp. 1348-1357.
Elbert, Donald L., et al., Protein delivery from materials formed by self-selective conjugate addition reactions; Journal of Controlled Release, vol. 76, (2001) pp. 11-25.
R. Kuroda M.D., et al., Treatment of a full-thickness articular cartilage defect in the femoral condyle of an athlete with autologous bone-marrow stromal cells; OsteoArthritis and Cartilage, 2006, vol. 15, pp. 226-231.
Christine Hiemstra, Rapidy in Situ-Forming Degradable Hydrogels from Dextran Thiols through Michael Addition, Biomacromolecules, 2007, pp. 1548-1556, vol. 8, No. 5.

* cited by examiner

*Primary Examiner* — Robert A Wax
*Assistant Examiner* — Olga V Tcherkasskaya
(74) *Attorney, Agent, or Firm* — Kirk Baumeister; Heather Champion Brady

(57) ABSTRACT

An absorbable PEG-based hydrogel prepared from a multi-arm-PEG-vinylsulfone having about 3 to about 8 arms and a multi-arm-PEG-R-sulfhydryl having about 3 to about 8 arms; where R is defined as an ester linkage, such as carboxylate ester, lactate ester, and isobutyrate ester have been disclosed. Additionally, sustained release compositions that are prepared from an absorbable PEG-based hydrogel and a protein have been disclosed which provide sustained release of proteins and peptides.

6 Claims, 7 Drawing Sheets

ABSORBABLE PEG-BASED HYDROGELS

RELATED APPLICATIONS

This application is a non-provisional filing of provisional application U.S. Pat. App. No. 61/369,818, filed Aug. 2, 2010.

FIELD OF THE INVENTION

The invention generally relates to the field of poly(ethylene glycol) (PEG)-based hydrogels. More specifically, the invention relates to absorbable PEG-based hydrogels that are useful for the sustained release of proteins.

BACKGROUND OF THE INVENTION

Injectable in situ forming hydrogel systems provide an attractive alternative to microspheres or implants as parenteral depot systems. Proteins represent a group of the most effective, natural and the fastest growing medicines for treatment of nearly 150 indications including various severe chronic conditions such as cancer, diabetes, hepatitis, leukemia and rheumatoid arthritis. A critical problem in protein therapy is that most protein drugs are currently administered by frequent injections due to their tissue impermeability and short in vivo life. The sustained release of proteins via in situ forming hydrogel systems has a number of advantages, such as ease of administration (less invasive compared to implants), simple fabrication method, ease of manufacturing, low cost of goods and the like. Also, sustained local release of proteins and other pharmaceutical agents provides improving bioavailability, reducing risk of systemic side effects, improving patient compliance and allowing the highest concentration of drug at disease site. One of the challenging issues in local drug delivery is the risk of infection, discomfort, and pain associated with frequent injections. Therefore, the number of injections per year should be reduced to a minimum.

PEG-based hydrogels have been prepared using Michael-type addition reaction such as, PEG-thiol or PEG-amine reacting with PEG-activated ester (NHS) or PEG-acrylate. These systems are typically nonabsorbable, the gelation times are not fast enough, and the reactions can result in unwanted small molecules as a secondary by product. Furthermore, the PEG-NHS compound may react with protein drugs due to the activated ester that reacts with amino groups to form an amide bond. Similarly, PEG-based hydogels have been prepared using 4-armPEG-vinylsulfone and linear PEG-estersulfhydryl. However, such PEG-based hydrogels absorb too quickly, within 5 days (S. Zustiak and J. Leach, "Hydrolytically Degradable Poly(Ethylene Glycol) Hydrogel Scaffolds with Tunable Degradation and Mechanical Properties", Biomacromolecules 2010, 11, 1348-1357), for example.

Therefore there is a need for an improved, fast forming PEG-based hydrodgel for a sustained release composition for proteins which is absorbable and yet can exhibit sustained release over a prolonged periods of time, for example greater than or equal to one month.

SUMMARY OF THE INVENTION

We disclose an absorbable PEG-based hydrogel prepared from a multi-arm-PEG-vinylsulfone having about 3 to about 8 arms and a multi-arm-PEG-R-sulfhydryl having about 3 to about 8 arms; where R is an ester linkage, such as carboxylate ester, lactate ester, and isobutyrate ester. We also disclose sustained release compositions that are prepared from an absorbable PEG-based hydrogel and a protein.

DETAILED DESCRIPTION OF THE INVENTION

Figure 1:
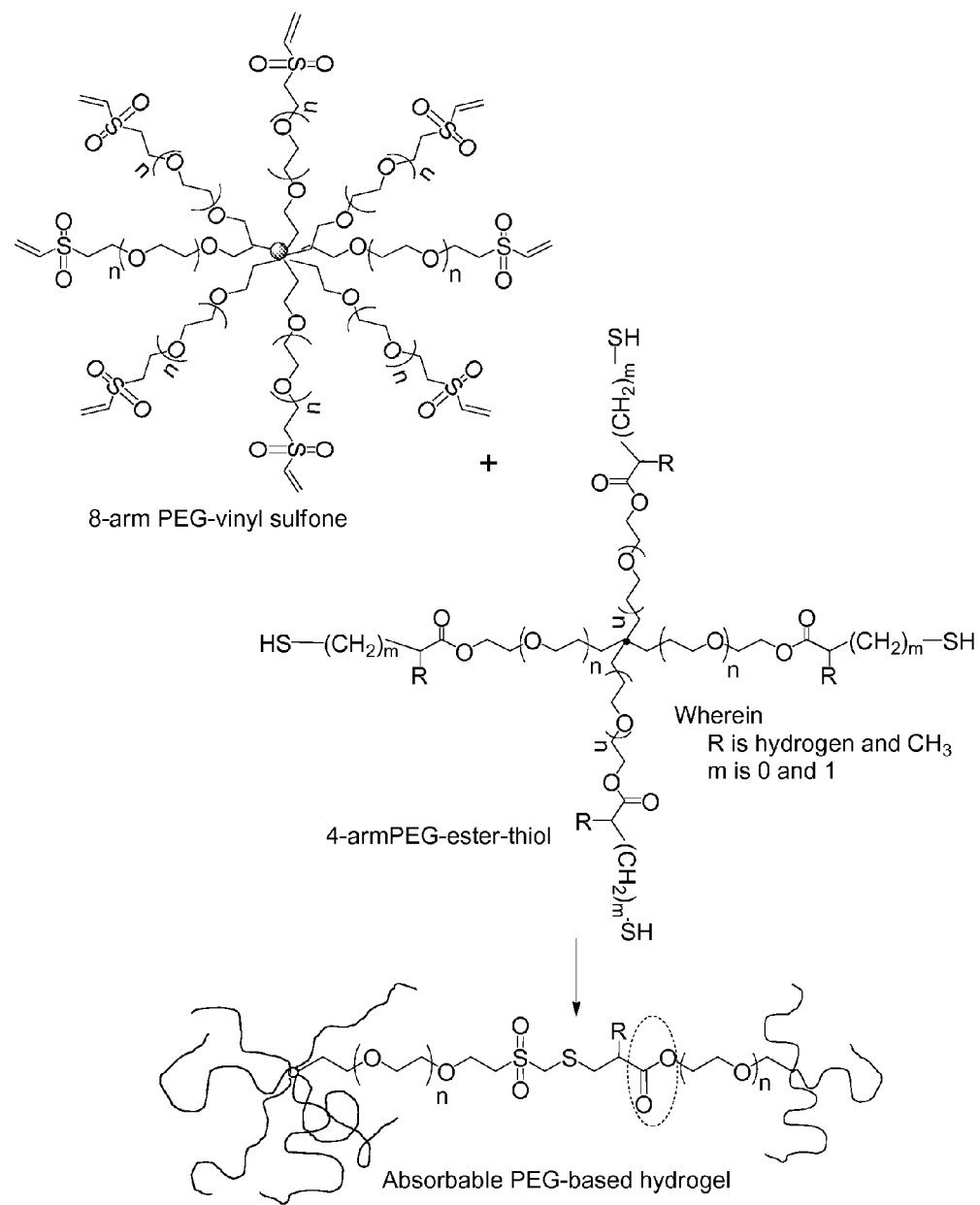
FIG. 1. Schematic drawing of absorbable PEG-based hydrogels.

We describe herein absorbable poly(ethylene glycol) (PEG)-based hydrogels comprising the reaction product of a multi-arm-PEG-vinylsulfone (-VS) having from about 3 arms to about 8 arms and a multi-arm-PEG-R-sulfhydryl (-SH) (-SH is also known as thiol) having from about 3 arms to about 8 arms and where R is an ester linkage including, but not limited to carboxylate ester (also known as ester), lactate ester (also known as lactic ester), and isobutyrate ester (also known as isobutyric ester). An exemplary embodiment of the reaction of a multi-arm-PEG-vinylsulfone with a multi-arm-PEG-R-sulfhydryl is shown in FIG. 1. The ester linkage, which enables the hydrogel to be absorbable, is circled in the reaction product. This absorbable PEG-based hydrogel is useful in the field of drug delivery, where the in situ formed hydrogel can entrap a protein and release the agent over time as the hydrogel degrades, which is described in further detail below.

Absorbable means that the PEG-based hydrogel readily breaks down or degrades and is either absorbed by the body, or passed by the body. More particularly, the PEG-based hydrogel degradation products do not elicit permanent chronic foreign body reaction, because they are absorbed by the body or passed from the body, such that no permanent trace or residual of the degradation products is retained by the body.

A hydrogel is a continuous solid network enveloped in a continuous liquid phase. Hydrogels possess a degree of flexibility very similar to natural tissue, due to their significant water content. Hydrogels described herein are made of branched polymer chains that are covalently crosslinked.

The multi-armed PEG-VS and the multi-armed PEG-SH may be tailored to increase or decrease the crosslink density, the molecular weight, and the rate of degradation of the absorbable PEG-based hydrogel. The crosslink density may be varied by increasing or decreasing the number of PEG arms. The molecular weight of the PEG arms may also be varied. The molecular weight of the multiarm-PEG must be such that when the hydrogel degrades into degradation products the degradation products may be cleared by the kidney. Additionally, the type of ester linkage may be chosen to vary how long it takes for the hydrogel to breakdown.

The multi-arm-PEG-VS may have from about 3 arms to about 8-arms. In one embodiment, the multi-arm-PEG-VS has 4-arms. In another embodiment, the multi-arm-PEG-VS has 8 arms. The multi-arm-PEG-VS may have molecular weight of about 10 kDa to about 40 kDa. In one embodiment, the multi-arm-PEG-VS may have a molecular weight of about 10 kDa.

The multi-arm-PEG-R-SH may have from about 3 arms to about 8-arms, where R is an ester linkage including, but not limited to carboxylate ester, lactate ester, and isobutyrate ester. In one embodiment, the multi-arm-PEG-R-SH has 4-arms. The multi-arm-PEG-R-SH may have molecular weight of about 2,000 Da to about 40 kDa. In one embodiment, the multi-arm-PEG-R-SH may have molecular weight of about 10 kDa.

The PEG-based hydrogel is formed by the Michael addition reaction of multi-arm-PEG-VS with the multi-arm-PEG-R-SH. The multi-arm-PEG-VS and multi-arm-PEG-R-SH are each dissolved in separate aqueous solutions in a concentration of from about 5% (w/v) to about 40% (w/v). In one embodiment, multi-arm-PEG-VS and multi-arm-PEG-R-SH are each dissolved in separate aqueous solutions in a concentration of about 20% (w/v). We define aqueous solution as water or buffered water, including, but not limited to phosphate buffered saline, citrate buffer, and boric acid based buffer. In the case of a buffered water solution the pH is in the range of from about 5.5 to about 11.0. In one embodiment, the pH is in the range of from about 7.4 to about 8.5.

The separate multi-arm-PEG-VS and multi-arm-PEG-R-SH solutions are then mixed together and react to form the absorbable PEG-based hydrogel. The amount of multi-arm-PEG-VS solution mixed with multi-arm-PEG-R-SH solution is calculated such that the mole ratio of multi-arm-PEG-VS to multi-arm-PEG-R-SH is from about 1:1 to about 1:2. In one embodiment, the mole ratio of multi-arm-PEG-VS to multi-arm-PEG-R-SH is about 1:1.

The reaction of the multi-arm-PEG-VS and multi-arm-PEG-R-SH solutions is fast such that the gel forms and stays in place while complete gelation may take about 2 seconds to about 6 hours at 37° C. The gelation time and the time to complete gelation may be controlled by for example, the ratio of the reactants, the concentration of the reactants in aqueous solutions, the temperature, and the pH of the solution as described above. One of skill in the art will be able to identify the appropriate conditions in order achieve gelation in the desired timeframe.

The absorbable PEG-based hydrogel described herein is useful as a sustained release composition for proteins. As defined herein, proteins include polypeptides (i.e. antibody), oligopeptides, and peptides. These terms shall be used interchangeably and shall not be limited as to any particular molecular weight, peptide sequence or length, field of bioactivity or therapeutic use unless specifically stated.

Proteins that are used to treat various chronic conditions may benefit from the sustained release composition as described herein. Suitable proteins that are administered for the treatment of chronic conditions, include, but are not limited to interferons, insulin, colony stimulating factors, erythropoietin (EPO), anti-TNF antibodies (e.g. Remicade), anti-IL-6 antibodies, human immunoglobulin G (hIgG), Factor VIII, insulin, and the like. The in vivo life of some protein drugs are limited to hours or even minutes after injection, far from sufficient to exert biological functions in vivo. Such proteins typically have a low therapeutic index and may benefit from an absorbable PEG-based hydrogel sustained release composition. Absorbable PEG-based hydrogel system can provide sustained levels of protein therapeutics and enhance the therapeutic index for proteins such as, interferons, Tumor necrosis factor, Activated Protein C (Xigris) and the like.

In one embodiment, the protein is an anti-IL-6 antibody. In another embodiment, the anti-IL-6 antibody is described in U.S. Pat. No. 7,560,112, hereby incorporated by reference herein in its entirety.

The protein can be incorporated into the hydrogel in various ways to form the sustained release composition. The agent can be added to the multi-arm-PEG-VS solution, to the multi-arm-PEG-R-SH solution, added as a separate aqueous solution, or as a neat powder or liquid upon combining the PEG solutions. The agent is entrapped in the hydrogel upon the mixing of the separate solutions together. The amount of protein present in the sustained release composition depends upon the potency of the protein and the desired amount of the protein to be delivered. For example, the protein may be present in the sustained release composition in an amount of from about 0.01 wt % to about 40 wt % of the total weight of the multi-arm-PEG-VS and the multi-arm-PEG-R-SH.

The sustained release of the protein from the sustained release composition may be accomplished for a time of from about 2 days to about 180 days. In one embodiment, the sustained release of the protein from the sustained release composition may be accomplished for a time of from about 10 days to 50 days. The sustained release of the protein may be controlled by changing the number of arms in the PEG-VS and PEG-R-SH, selecting faster degrading ester linkages (R groups), and by adding excipients to the composition.

Optionally, excipients may be added to adjust the sustained release profile of the protein. Suitable excipients include, but are not limited to polyvinylpyrrolidone (PVP) and cyclodextrins. Suitable cyclodextrins are those that are available commercially as a pharmaceutical grade material such as, alpha-cyclodextrin, beta-cyclodextrin, gamma-cyclodextrin, delta-cyclodextrin, hydroxypropyl-beta-cyclodextrin, sulfobutylether-beta-cyclodextrin, and the like.

The excipient can be incorporated into the sustained release composition in various ways. The excipient can be added to the multi-arm-PEG-VS solution, to the multi-arm-PEG-R-sulfhydryl solution, or added to a separate protein solution. The amount of excipient present in the sustained release composition depends upon the desired sustained release profile, for example, the excipient can be present in the range of from about 0.5% wt to about 30% wt. of the total weight of the multi-arm-PEG-VS and the multi-arm-PEG-R-SH.

The sustained release composition may be provided, for example as three separate septum-capped vials containing the sterile components of the sustained release composition; one vial containing a solution of multi-arm-PEG-VS, one vial containing a solution of multi-arm-PEG-R-SH, and one vial containing the protein solution. The multi-arm PEG solutions may be added to the protein vial using aseptic sterile techniques such as drawing up into a syringe and injecting into the protein vial. Subsequently, the contents may be mixed quickly and vigorously, by vortexing for example, drawn up into a syringe and then injected into the patient either subcutaneously or intramuscularly. The mixture will then gel in situ to provide the sustained release composition.

Alternatively, the protein maybe provided in the multi-arm-PEG-R-SH solution. Therefore the multi-arm-PEG-R-SH/protein solution and the multi-arm-PEG-VS may be administered by using a conventional dual mixing syringe and simultaneously injected into the patient either subcutaneously or intramuscularly. The mixture will then gel in situ to provide the sustained release composition. Other conventional means of providing the sterile components of the sustained release composition and conventional methods of injection may also be used in conjunction with the invention as described herein.

Alternatively, the sustained release composition may be pre-made and implanted. The multi-arm-PEG-R-SH and multi-arm-PEG-VS solutions may be combined with the protein solution, and subsequently mixed quickly and vigorously, by vortexing for example. The mixture may be poured into a suitable mold, such as a dish or pan, and then allowed to cure. The cured hydrogel may either be cut into samples or used as is. The sustained release composition in pre-made hydrogel form may then be implanted subcutaneously, for example, thereby providing sustained release of the protein.

The sustained release composition is useful for the sustained release of proteins from the PEG-based hydrogel. The PEG-based hydrogel described herein may provide sustained release of a protein for up to 50 days or longer. The ester linkages allow the composition to break down and become absorbed or excreted by the body. Therefore, there will be a reduced number of injections for the patient and in the case of multiple injections over time the material will not build up in the injection locations.

The following examples are illustrative of the principles and practice of this invention, although not limited thereto. Numerous additional embodiments within the scope and spirit of the invention will become apparent to those skilled in the art once having the benefit of this disclosure.

EXAMPLES

Example 1

Preparation of a Sustained Release Composition Prepared from 4-arm-Peg-Ester-Sulfhydryl (-ESH) and 8-arm-PEG-vinylsulfone (-VS) with anti-IL-6 Antibody 45.5 mg of 4-arm-PEG-SH ($PEG_{10k}$-$(ESH)_4$, Jenkem Technology USA, Allen, Tex.) were dissolved in 239 μL of 20 mM sodium phosphate buffer (pH 8.5) in a screw top vial at room temperature with vortex mixing. Separately, 22.3 mg of 8-arm-PEG-VS (8-arm$PEG_{10k}$-$(VS)_8$, Jenkem Technology USA, Allen, Tex.) were dissolved in 100 μL of 20 mM sodium phosphate buffer (pH 8.5) at room temperature with vortex mixing. Anti-IL-6 antibody was provided in a histidine buffer solution (pH=5.5) in a concentration of 50.7 mg/mL (Centocor, Radnor, Pa.). The two PEG solutions and the antibody solution were combined together and mixed by vortexing. After vortexing for 10 s, the solution mixture was poured into an aluminum pan and cured for 1 hr at 37° C. The procedure was repeated adding 3.39 mg (5% wt %) and 6.78 mg (10 wt %) antibody to total weight of PEG-VS and PEG-ESH, respectively. The hydrogels were stored at −20° C. until use. The hydrogels were disc-shaped having dimensions of approximately 0.55 mm in diameter and 0.21 mm in height.

Example 2

Preparation of a Sustained Release Composition Prepared from 4-arm-PEG-lactic ester-sulfhydryl (-LESH) and 8-arm-PEG-VS with Anti-IL-6 Antibody 41.4 mg of 4-arm-PEG-LESH ($PEG_{10k}$-$(LESH)_4$, Jenkem Technology USA) were dissolved in 220 μL, of 20 mM sodium phosphate buffer (pH 8.5) in a screw top vial at room temperature with vortex mixing. Separately, 22.3 mg of 8-arm-PEG-VS (8-arm$PEG_{10k}$-$(VS)_8$, Jenkem Technology USA) were dissolved in 100 μL, of 20 mM sodium phosphate buffer (pH 8.5) at room temperature with vortex mixing. Anti-IL-6 antibody was provided in a histidine buffer solution (pH=5.5) in a concentration of 50.7 mg/mL (Centocor, Radnor, Pa.). The two PEG solutions and the antibody solution were combined together and mixed by vortexing. After vortexing for 10 s, the solution mixture was poured into an aluminum pan and cured for 1 hr at 37° C. The procedure was repeated adding 3.19 mg (5% wt %) and 6.37 mg (10 wt %) antibody to total weight of PEG-VS and PEG-R-SH, respectively. The hydrogels were stored at −20° C. until use. The hydrogels were disc-shaped having dimensions of approximately 0.55 mm in diameter and 0.21 mm in height.

Example 3

Preparation of a Sustained Release Composition Prepared from 4-arm-Peg-isobutyric ester-sulfhydryl (-IBESH) and 8-arm-PEG-VS with Anti-IL-6 Antibody 43.2 mg of 4-arm-PEG-IBESH ($PEG_{10k}$-$(IBESH)_4$, Jenkem Technology USA) was dissolved in 230 μL of 20 mM sodium phosphate buffer (pH 8.5) in a screw top vial at room temperature with vortex mixing. Separately, 22.3 mg of 8-arm-PEG-VS (8-arm$PEG_{10k}$-$(VS)_8$, Jenkem Technology USA) were dissolved in 100 μL of 20 mM sodium phosphate buffer (pH 8.5) in a screw top vial at room temperature with vortex mixing. Anti-IL-6 antibody was provided in a histidine buffer solution (pH=5.5) in a concentration of 50.7 mg/mL (Centocor, Radnor, Pa.). The two PEG solutions and the antibody solution were combined together and mixed by vortexing. After vortexing for 10 s, the solution mixture was poured into an aluminum pan and cured for 1 hr at 37° C. The procedure was repeated adding 3.27 mg (5% wt %) and 6.55 mg (10 wt %) antibody to total weight of PEG-VS and PEG-LESH, respectively. The hydrogels were stored at −20° C. until use. The hydrogels were disc-shaped having dimensions of approximately 0.55 mm in diameter and 0.21 mm in height.

Example 4

Preparation of a Sustained Release Composition Prepared from 4-arm-PEG-ESH and 4-arm-PEG-VS with Anti-IL-6 Antibody 45.5 mg of 4-arm-PEG-ESH ($PEG_{10k}$-$(ESH)_4$, Jenkem Technology USA) was dissolved in 252 μL of 20 mM sodium phosphate buffer (pH 8.5) in a screw top vial at room temperature with vortex mixing. 43.5 mg of 4-arm-PEG-VS (4-arm$PEG_{10k}$-$(VS)_4$, Jenkem Technology USA) were dissolved in 200 μL of 20 mM sodium phosphate buffer (pH 8.5) in a screw top vial at room temperature with vortex mixing. Anti-IL-6 antibody was provided in a histidine buffer solution (pH=5.5) in a concentration of 50.7 mg/mL (Centocor, Radnor, Pa.). The two PEG solutions and the antibody solution were combined together and mixed by vortexing. After vortexing for 10 s, the solution mixture was poured into an aluminum pan and cured for 1 hr at 37° C. The procedure was performed adding 4.45 mg (5% wt %) antibody to total weight of PEG-VS and PEG-ESH, respectively. The procedure was repeated without antibody solution to make a PEG-based hydrogel (no antibody). The hydrogels were stored at −20° C. until use. The hydrogels were disc-shaped having dimensions of approximately 0.55 mm in diameter and 0.21 mm in height.

Example 5

Figure 2:
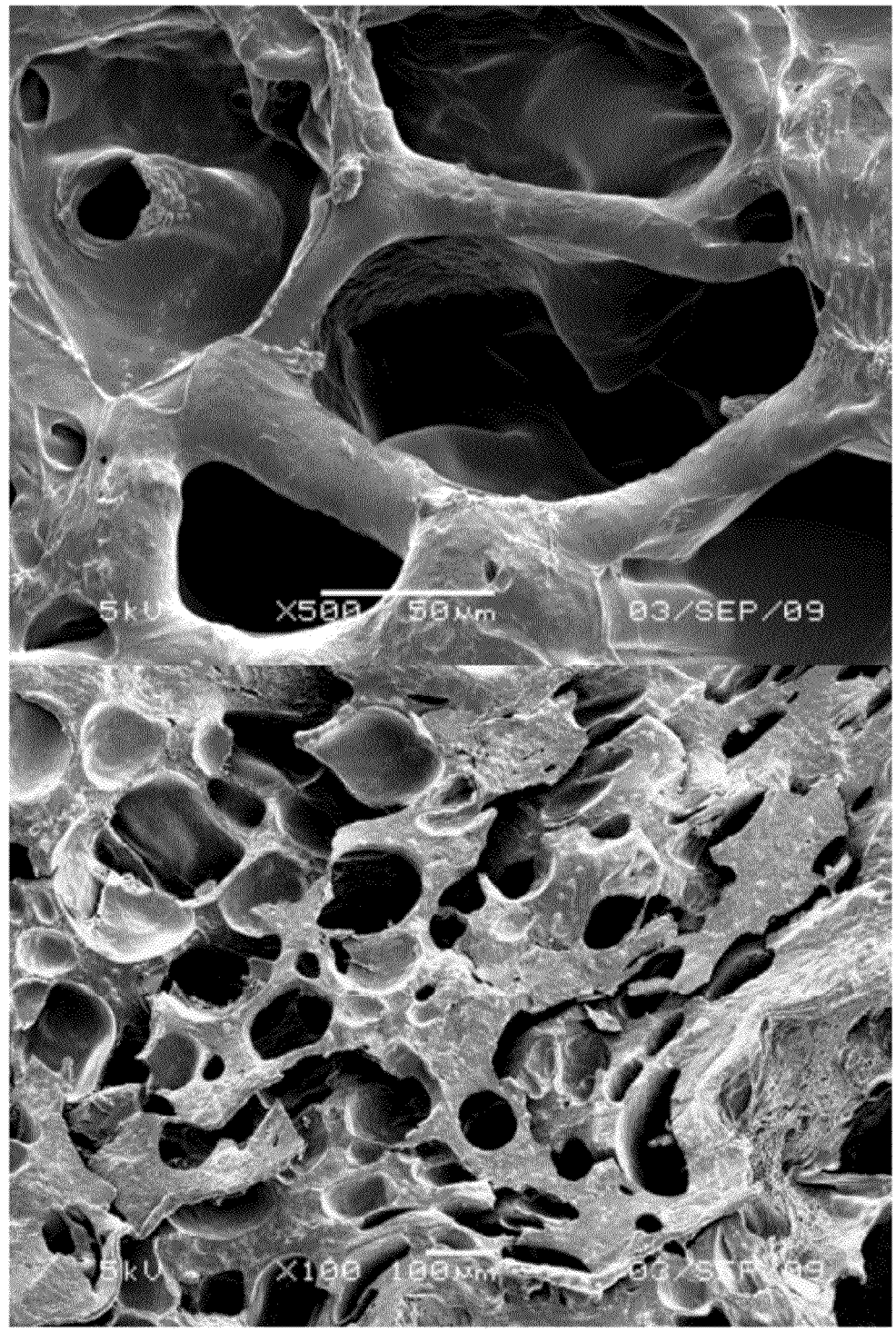
FIG. 2. SEM images of absorbable PEG-based hydrogels.

Morphology of Lyophilized Absorbable PEG-Based Hydrogel and Sustained Release Composition Containing Anti-IL-6 Antibody Sustained release composition having anti-IL-6 antibody and PEG-based hydrogel (without antibody) made as described in Example 4 were dried by lyophilization to remove the water from the samples. Each sample was evaluated for morphology by scanning electron microscopy using a JSM-5900LV SEM. The SEM micrographs show that the outside surface of the two lyophilized hydrogel samples had similar morphology. The SEM images of the outside surface of cylinder-shaped structures showed a textured sample surface with some large pores ranging in size from approximately 10 to 50 microns across the surface. The cross-sectional images indicate a foam-like matrix with an open porous structure. In addition, under high magnification, a population of smaller pores was also observed having a pore diameter of 3 microns. Exemplary cross-sectional views of the foam under two different magnifications are shown in FIG. 2. Therefore, we have shown that the hydrogels have an open interconnected network of pores of varying sizes.

Example 6

Rheology of Absorbable PEG-Based Hydrogels

Figure 3:
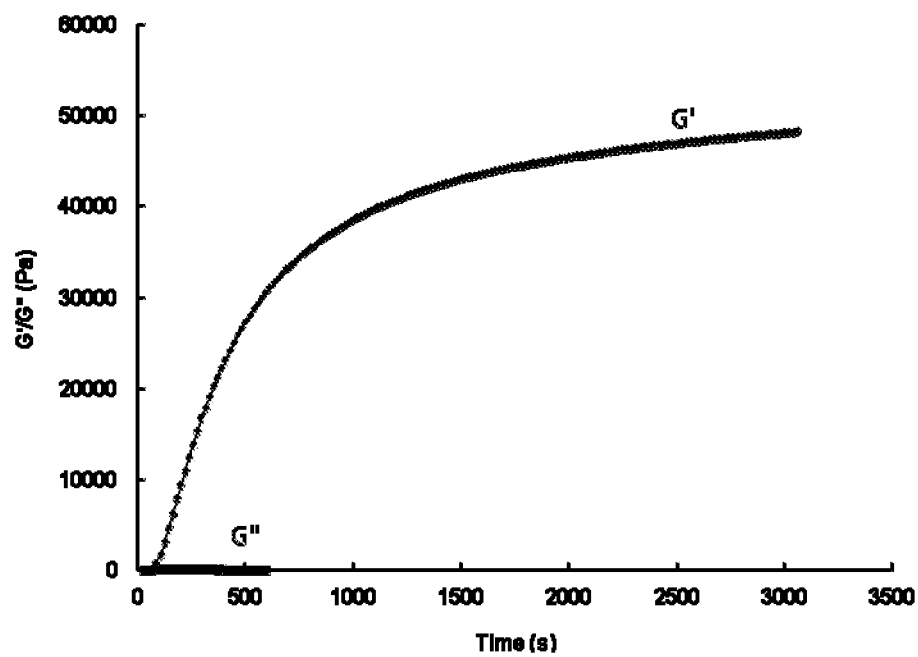
FIG. 3. Rheology analysis to measure mechanical properties of hydrogels.

Rheology experiments were performed on the PEG-based hydrogel solutions to evaluate the physical strength of the hydrogel. A controlled strain rheometer, ARES (TA Instruments, Inc., New Castle, Del.) equipped with parallel plates and peltier heating was used for the rheology testing. Fixtures were preheated to 25° C. and equilibrated for about 15 minutes, the PEG solutions were prepared as described in Example 1. The solutions were combined (without antibody) and vortexed as described in Example 1 and then loaded between the two parallel plates. Immediately after sample loading, the sample was subjected to a dynamic time sweep test at angle frequency=1 rad/s, strain=1%, and temperature T=25° C. The storage modulus (G'), loss modulus (G"), and loss tangent was collected with time, results are shown in FIG. 3. Dynamic strain sweep tests were performed after the time sweep to ensure the experiment was performed in the linear viscoelastic region. Finally, a dynamic frequency sweep was performed to investigate the viscoelastic response to different angle frequency. FIG. 3 shows that the hydrogel possesses maximum storage modulus (G') of around 50,000 Pa, which is significantly higher than other known absorbable PEG-based hydrogels (i.e. (G') of from about 1,000 to about 3,000 Pa, S. Zustiak and J. Leach, "Hydrolytically Degradable Poly(Ethylene Glycol) Hydrogel Scaffolds with Tunable Degradation and Mechanical Properties", Biomacromolecules 2010, 11, 1348-1357).

Example 7

In Vitro Release Study of Sustained Release Composition Prepared from 4-arm-PEG-ester-sulfhydryl (-ESH) and 8-arm-PEG-vinylsulfone (-VS) with Anti-IL-6 Antibody Sustained release compositions of 4-arm-PEG-ester-sulfhydryl (-ESH) and 8-arm-PEG-vinylsulfone (-VS) with anti-IL-6 antibody prepared as described in Example 1 were submerged in 5 mL of PBS and placed in an incubator which was maintained at 37° C. At pre-determined time intervals, 100 µL of buffer were withdrawn and placed in a high performance liquid chromatography (HPLC) vial having a polypropylene small volume insert. A size exclusion chromatography (SEC) method was used to quantify the concentration of anti-IL-6 antibody in the buffer solution against protein standard. Briefly, a SEC column (Part number G3000SW-XL, 7.8×300 mm, 5 µm, Tosoh Biosep, Japan) was used to separate anti-IL-6 antibody using an Agilent 1100 HPLC (Foster City, Calif.) with 100 µL sample loop and 10 mm flow cell. The mobile phase was 0.2M Sodium Phosphate Buffer (pH 6.8±0.05), the injection volume was 20 µL at room temperature, and the flow rate was 1 ml/min. The antibody was monitored at 254 nm. Quantification of antibody concentration was against known protein standards. The amount of accumulative release and fraction of release of the antibody was calculated based on theoretical protein loading in the hydrogel and the amount released at each time point.

Figure 4:
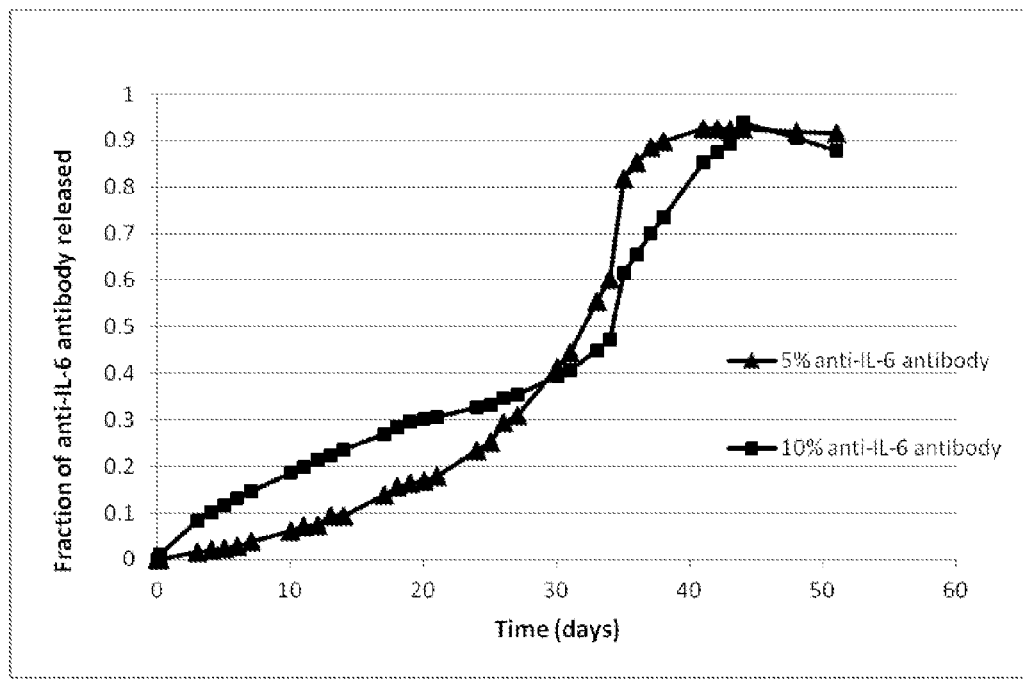
FIG. 4. In vitro release study of an anti-IL-6 antibody from the absorbable PEG-based hydrogel (4-armPEG10k-ESH with 8-armPEG10k-VS).

Release profiles of the 5 wt % and 10 wt % anti-IL-6 antibody sustained release composition are shown in FIG. 4. The antibody was released from the hydrogels for a period of 50 days.

Example 8

In Vitro Bioassay of Sustained Release Compositions Prepared from 4-arm-PEG-ester-sulfhydryl (-ESH) and 8-arm-PEG-vinylsulfone (-VS) with Anti-IL-6 Antibody 5 wt % of anti-IL-6 antibody to total PEG-VS and PEG-ESH sustained release composition was prepared as described in Example 1 and tested in duplicate. The samples were submerged in 5 mL of phosphate buffered saline (PBS) at 37° C. and the supernatant was tested by HPLC daily for concentration of antibody. Once the concentration of antibody reached 100 micrograms/mL, the supernatant was tested in the bioassay. In addition, two control samples were tested. The first control sample was an empty PEG-based hydrogel prepared using the methods of Example 1 but without antibody and tested in duplicate. The empty PEG-based hydrogels were submerged in 5 mL of phosphate buffered saline (PBS) at 37° C. the PBS solution was then spiked with anti-IL-6 antibody solution (see Example 1) to have a concentration of 100 micrograms/mL in the PBS. The second control sample was the anti-IL-6 antibody standard solution described in Example 1.

A standard 7TD1 neutralization assay was used to evaluate IL-6 dependent proliferation of a murine hybridoma cell line. 7TD 1 cells were plated into a 96 well plate at 200 cells per well. Antibodies, diluted in minimal essential medium (MEM) media, were added to the wells followed by the addition of human IL-6 to a final concentration of 500 µg/ml and plates were incubated in a tissue culture incubator for 64-72 hours. At that time, 50 µl of cell lysis buffer from the ATPlite kit (Packard Bioscience, Meriden, Conn.) were added to all wells and the plates were agitated for 3 minutes. 50 µl of ATPlite substrate were added and the covered plates were shaken for 1 minute. Chemiluminescence was determined on a luminometer.

Bioassay results are shown in Table 1. $EC_{50}$ is defined as the concentration of antibody that provokes a response halfway between the baseline (Bottom) and maximum response (Top). All $EC_{50}$ values were similar in value (within experimental error), which is an indication that the antibody biological activity is unaffected by the hydrogel.

TABLE 1

$EC_{50}$ of anti-IL-6 antibody from hydrogels were similar to anti IL-6 antibody standard.

| Test Sample | $EC_{50}$ |
|---|---|
| Anti-IL-6 antibody from 5 wt % sustained release composition | 0.002534 |
| Anti-IL-6 antibody from 5 wt % sustained release composition duplicate | 0.002985 |
| First control- empty PEG-based hydrogel spiked with 5 wt % anti-IL-6 antibody | 0.002303 |
| First control- empty PEG-based hydrogel spiked with 5 wt % anti-IL-6 antibody duplicate | 0.005047 |
| Second control- anti-IL-6 antibody standard | 0.00561 |

Example 9

Preparation of Sustained Release Compositions of Absorbable PEG-Based Hydrogels and Anti-IL-6 Antibody with polyvinylpyrrolidone (PVP) as an Excipient 45.5 mg of 4-arm-PEG-ESH ($PEG_{10k}$-$(ESH)_4$, Jenkem Technology USA) were dissolved in 239 µL of 20 mM sodium phosphate buffer (pH 8.5) in a screw top vial at room temperature with vortex mixing. Separately, 22.3 mg of 8-armPEG-VS (8-armPEG$_{10k}$-$(VS)_8$, JenKem) were dissolved in 100 µL of 20 mM sodium phosphate buffer (pH 8.5) in a screw top vial at room temperature with vortex mixing. 6.78 mg of PVP (Mw=25,000, BASF) were dissolved in the 8-armPEG-VS solution. An antibody solution was also prepared having 2.71 mg (2% wt %) of antibody in sodium phosphate buffer (pH 8.5). And then, the two PEG solutions were mixed together followed by adding the antibody solution. A control sustained release composition was prepared in the same manner only without the PVP. The combined solutions were thoroughly mixed by vortexing for 10 s, then poured into an aluminum pan and cured for 1 hr at 37° C. The hydrogels were stored at −20° C. until use. The disc shaped hydrogel was had dimensions of approximately 0.55 mm diameter and 0.21 mm in height.

Release studies were conducted on these sustained release compositions by the methods described in Example 7. Data of the release studies is shown in FIG. 5.

Figure 5:
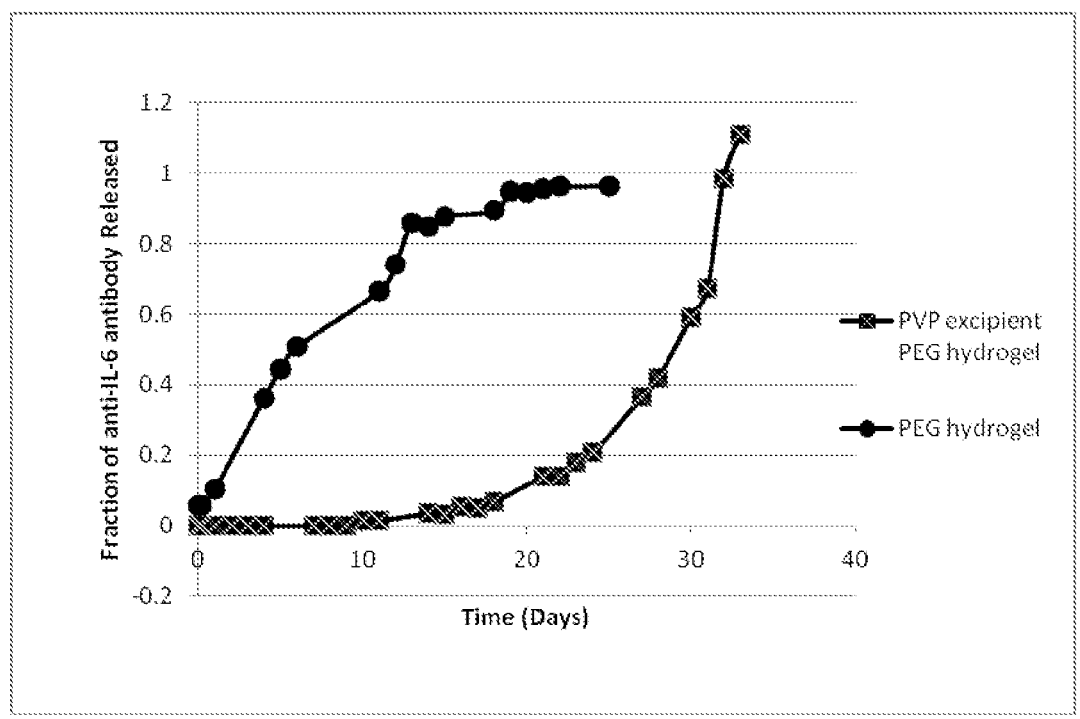
FIG. 5. In vitro release study of an anti-IL-6 antibody from absorbable PEG-based hydrogel with PVP as an excipient.

PVP can modulate the rate of release of the antibody from the hydrogels as shown in FIG. 5. PVP prolonged and delayed the release of the antibody. PVP increased the duration of the antibody release from 25 days (no PVP) to 32 days and also delayed the majority of the antibody release to 25 days (less than 0.2 fraction release before 25 days). One of skill in the art may adjust the amount of PVP present in the sustained release composition to obtain the desired release profile.

Example 10

Preparation of a Sustained Release Composition of Absorbable PEG-Based Hydrogels and Anti-IL-6 Antibody with Cyclodextrin (CD) as an Excipient 45.5 mg of 4-armPEG-ester-SH ($PEG_{10k}$-$(ESH)_4$, Jenkem Technology USA) were dissolved in 239 µL of 20 mM sodium phosphate buffer (pH 8.5) a screw top vial at room temperature with vortex mixing. Separately, 22.3 mg of 8-armPEG-VS (8-arm-PEG$_{10k}$-$(VS)_8$, JenKem) were dissolved in 100 µL of 20 mM sodium phosphate buffer (pH 8.5) a screw top vial at room temperature with vortex mixing. In yet another vial, cyclodextrin (Sigma, St. Louis, Mich.) was dissolved in 20 mM sodium phosphate buffer (pH 8.5) to make a 2% (wt) solution. Five different CDs were employed, alpha-CD, beta-CD, gamma-CD, hydroxypropyl (HP)-beta-CD and hydroxypropyl(HP)-gamma-CD. The CD solutions were added to the different hydrogel precursor solutions in order to test the affect of the different threading methods. For example, if CD solutions added to antibody solution, it is called threading the antibody (T-antibody). Three threading methods were employed by adding 150 µL of CD solution to either 4-armPEG-ester-SH, 8-armPEG-VS or antibody solution. The two PEG solutions were combined together followed by adding 2.71 mg (2 wt %) of antibody (anti-IL-6 antibody) to the combined PEG solution. After vortexing for 10 s, the solution mixture was poured into an aluminum pan and cured for 1 hr at 37° C. The disc shaped hydrogels had dimensions of 0.55 mm diameter and 0.21 mm in height. The hydrogel was stored at −20° C. until use. In vitro release studies were conducted as described in Example 7.

Figure 6:
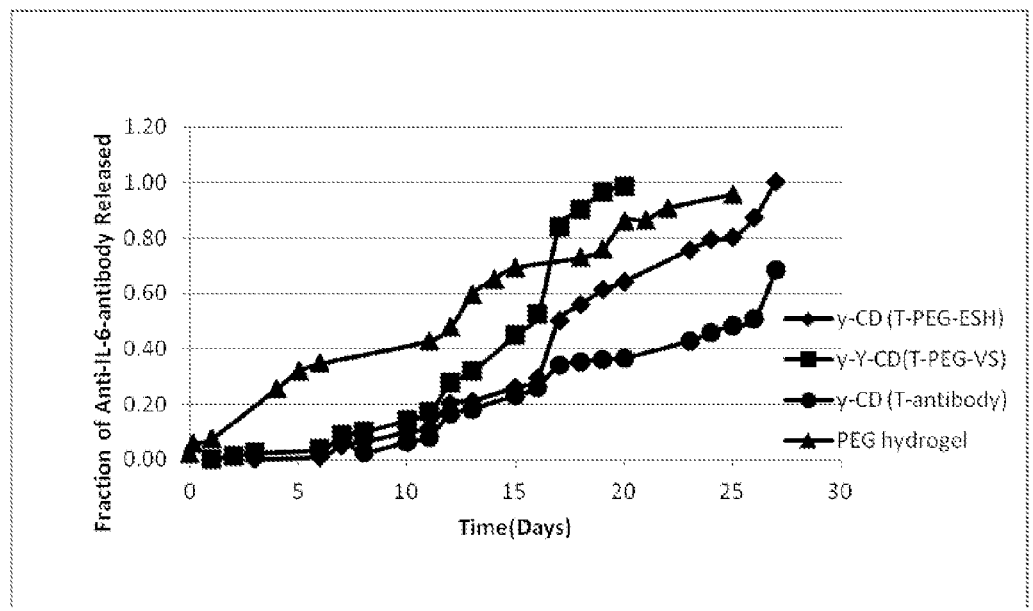
FIG. 6. In vitro release study of an anti-IL-6 antibody from absorbable PEG-based hydrogel with gamma-cyclodextrin as an excipient.

Gamma-CD can modulate the rate of release of the antibody from the hydrogels as shown in FIG. 6. Gamma-CD enabled the controlled and prolonged release of the antibody from the PEG-based hydrogels. The threading method also impacted the rate of antibody release from the PEG-based hydrogels. The sustained release composition made where T-VS was the threading method (threading PEG-VS) resulted in the slowest rate of release, 0.7 fraction of total loaded antibody was released over 27 days.

Example 11

Gelation Time Measurement for Sustained Release Compositions of Absorbable PEG-Based Hydrogels and Anti-IL-6 Antibody Using Rheology and Visual "Flip-Pan" Method Rheology experiments were performed on the PEG-based hydrogel solutions with excipients to evaluate the gel point and time for complete gelation of the hydrogel. A controlled strain rheometer, ARES (TA Instruments, Inc.) equipped with parallel plates and peltier heating was used for the rheology testing. Fixtures were preheated to 25° C. and equilibrated for about 15 minutes, sample was then loaded between the two parallel plates. Two PEG precursor solutions, as described in Example 4 without antibody was poured immediately after mixing the PEG precursor solutions. The samples were subjected to a dynamic time sweep test at angle frequency=1 rad/s, strain=1%, and temperature T=25° C. The storage modulus (G'), loss modulus (G"), and loss tangent were collected over time. Dynamic strain sweep tests were performed after the time sweep to ensure all the experiments were performed in the linear viscoelastic region. The gelation time from the rheology test was taken as the point at which the viscosity is greater than 1000 Pa-s.

Another visual examination experiment was conducted to evaluate gelation of this PEG based system. The method was called "flip-pan" approach because it essentially was examining the gelation by flipping the sample pan. If there is no gelation, the sample will drip, if there is gelation, the sample will stay with the sample pan. By periodically flipping the pan and examining the gelation, gelation time was recorded for the formulations.

Gelation time measured by rheology and by "flip-pan" showed consistent results. Both methods showed that gelation occurs faster with higher pH and higher temperature. The PEG based hydrogel generally gelled within 20 min at room temperature (Table 2).

TABLE 2

Gelation time determined by rheology experiment and "flip-pan" method.

| | Gel Time by Rheology | | Gel time by Flip Pan | |
|---|---|---|---|---|
| pH | At 25° C. (min) | At 37° C. (min) | At 25° C. (min) | At 37° C. (min) |
| 7.8 | 8.0 | 5.5 | 14.0 | 12.0 |
| 8.0 | 8.7 | 8.7 | 7.0 | 6.0 |
| 8.5 | 15.8 | 15.8 | 4.0 | 2.5 |

Example 12

In Vivo Biocompatibility Study in Sprague Dawley Rat Gluteal Muscle Flap Model

A 28 day study was performed to evaluate the tissue reaction/biocompatibility of absorbable PEG-based hydrogels in a rat gluteal muscle flap model.

The test material was a pre-made absorbable PEG-based hydrogels (without antibody) were composed of 4-arm PEG-ester-SH (MW 10 kDa) and 4-arm PEG-VS (MW 10 kDa). Sample hydrogels were made in the manner as described in Example 4.

The test material was cut into approximately 6 mm diameter×1-2 mm thick discs and the discs were surgically implanted into the gluteal muscles of male Sprague Dawley rats using the gluteal "flap" method in a total of 12 animals (4 animals per period for days 3, 7, and 28). Both the left and right gluteal muscles were implanted with the test material with two implants per animal. All sites were examined grossly at the time of necropsy (details in the main study report), and then each implant site was preserved in 10% neutral buffered formalin fixative. Following fixation, single transverse sections were trimmed from all gluteal muscle implant sites. Sectioning of the muscle was from the approximate longitudinal midpoint of each specimen (i.e., the implants were [or had been, for absorbed sites] located in this approximate area). Gluteal muscle site cassettes were identified with the accession number, animal number and side (L or R). The trimmed specimens were submitted to Vet Path Services, Inc., Mason, Ohio for standard processing to paraffin embedment. Each block was sectioned then stained with hematoxylin and eosin, yielding one slide with one section per site. The prepared slides were read by a veterinary pathologist. The sites were generally evaluated histologically in a subjective to semi-quantitative manner. All sites were examined under normal and polarized light.

Based upon the histologic findings, absorbable PEG-based hydrogels were considered to be biocompatible. The test material had minimal to slight tissue reaction across the periods, trace muscle necrosis at day 3 and minimal muscle regeneration at days 7 and 28. The test material showed early evidence of absorption at day 7 and was essentially absorbed at day 28 with a slight residual macrophage infiltrate. The designation of "essentially absorbed" versus "total absorption" for the test material at day 28 was based upon the nature of the residual cellular infiltrate (macrophages with "foamy" cytoplasm) at all sites. This morphology was considered to represent a late stage in the absorption of the material (intracellular digestion). Therefore, we concluded that these absorbable PEG-based hydrogels are biocompatible.

Example 13

In Vitro Release Study of Sustained Release Composition Prepared from 4-arm-PEG-isobutyric ester-sulfhydryl (-IBESH) and 8-arm-PEG-vinylsulfone (-VS) with Anti-IL-6 Antibody Duplicate sustained release compositions of 4-arm-PEG-isobutyric ester-sulfhydryl (-IBESH) and 8-arm-PEG-vinylsulfone (-VS) with 10% anti-IL-6 antibody prepared as described in Example 3 were submerged in 5 mL of PBS and placed in an incubator which was maintained at 37° C. At pre-determined time intervals, 100 µL of buffer were withdrawn and placed in a high performance liquid chromatography (HPLC) vial having a polypropylene small volume insert. A size exclusion chromatography (SEC) method was used to quantify the concentration of anti-IL-6 antibody in the buffer solution against protein standard. Briefly, a SEC column (Part number G3000SW-XL, 7.8×300 mm, 5 µm, Tosoh Biosep, Japan) was used to separate anti-IL-6 antibody using an Agilent 1100 HPLC (Foster City, Calif.) with 100 µL sample loop and 10 mm flow cell. The mobile phase was 0.2M Sodium Phosphate Buffer (pH 6.8±0.05), the injection volume was 20 µL at room temperature, and the flow rate was 1 ml/min. The antibody was monitored at 254 nm. Quantification of antibody concentration was against known protein standards. The amount of accumulative release and fraction of release of the antibody was calculated based on theoretical protein loading in the hydrogel and the amount released at each time point.

Figure 7:
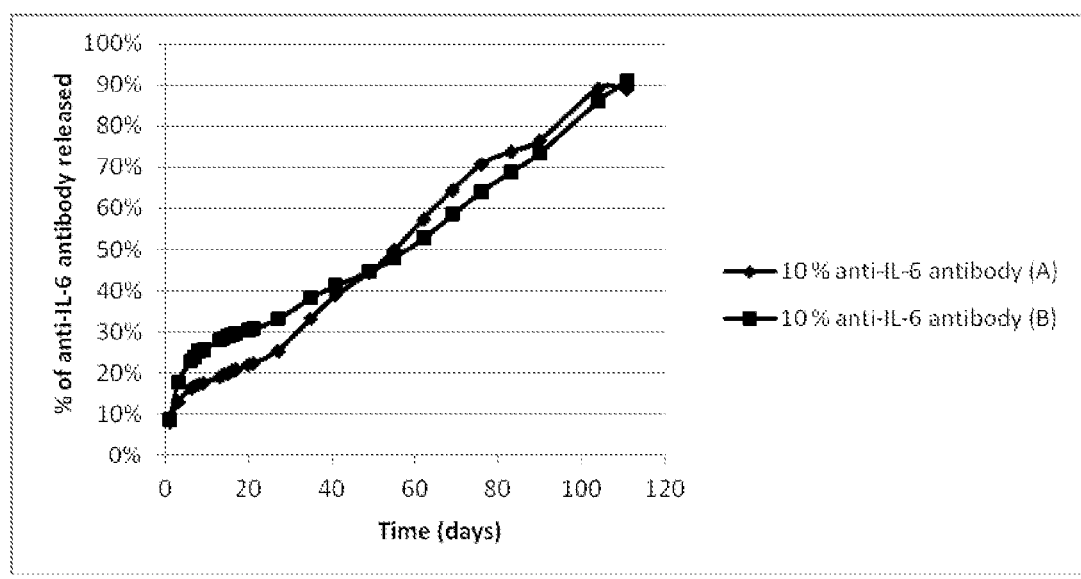
FIG. 7. In vitro release study of an anti-IL-6 antibody from absorbable PEG-based hydrogel ($PEG_{10k}$-$(IBESH)_4$ with $PEG_{10k}$-$(VS)_8$).

Release profiles of the 10 wt % anti-IL-6 antibody sustained release composition are shown in FIG. 7. The antibody was released from the hydrogels for a period of 120 days.

We claim:

1. A method of sustained release of a protein comprising the steps of:
   providing a sustained release composition comprising, a PEG-based hydrogel comprising, the reaction product of a multi-arm-PEG-vinylsulfone having about 3 to about 8 arms and a multi-arm-PEG-R-sulfhydryl having about 3 to about 8 arms; wherein R si an ester linkage selected from the group consisting of carboxylate ester, lactate ester, and isobutyrate ester; and a protein, implanting the sustained release composition, and releasing the protein from the composition for up to about 180 days.

2. The method of sustained release of a protein of claim 1 wherein the N-arm-PEG-vinylsulfone and the N-arm-PEG-R-sulfhydryl are in a ratio of from about 1:1 to about 1:2.

3. The method of sustained release of a protein of claim 1 wherein, the molecular weight of the PEG is from about 2000 Da to about 40 kDa.

4. The method of sustained release of a protein of claim 1 wherein the protein is an anti-IL-6 antibody.

5. The method of sustained release of a protein of claim 1, wherein the PEG-based hydrogel further comprises an excipient.

6. The method of sustained release of a protein of claim 5, where the excipient is cyclodextrin.

* * * * *